United States Patent [19]

Bouras

[11] Patent Number: 6,114,389
[45] Date of Patent: Sep. 5, 2000

[54] USE OF A PHARMACEUTICALLY ACCEPTABLE OXALATE DERIVATIVE FOR THE TREATMENT OF SKIN CONDITIONS

[75] Inventor: Elias Bouras, Bognor Regis, United Kingdom

[73] Assignee: Phytopharm plc, Godmanchester, United Kingdom

[21] Appl. No.: 08/973,159

[22] PCT Filed: May 15, 1996

[86] PCT No.: PCT/GB96/01157

§ 371 Date: Nov. 19, 1997

§ 102(e) Date: Nov. 19, 1997

[87] PCT Pub. No.: WO96/36324

PCT Pub. Date: Nov. 21, 1996

[30] Foreign Application Priority Data

May 19, 1995 [GB] United Kingdom .................... 9510162

[51] Int. Cl.⁷ .................................................... A61K 31/19
[52] U.S. Cl. ............................................................ 514/574
[58] Field of Search ................................................ 514/574

[56] References Cited

U.S. PATENT DOCUMENTS 5,175,006  12/1992  Matkovic et al. ....................... 514/492
5,639,459   6/1997  Bouras ................................. 424/195.1
5,648,389   7/1997  Gans et al. .............................. 514/557

FOREIGN PATENT DOCUMENTS

92/04896  4/1992  WIPO .
94/15574  7/1994  WIPO .

OTHER PUBLICATIONS

Robert Berkow et al.: "The Merck Manual of Diagnosis and Therapy". The Merck Research Laboratories, 1992, 16th Edition, pp. 1317, 2407–2411, 2435, 2441.

*Primary Examiner*—William R. A. Jarvis
*Attorney, Agent, or Firm*—Venable; George H. Spencer; Marina V. Schneller

[57] ABSTRACT

The invention provides a method for the treatment of a condition, disorder or a disease of the skin by administering a pharmaceutically acceptable oxalate. Preferably, the oxalate is a transition metal oxalate and the pharmaceutically acceptable carrier is an ointment.

32 Claims, No Drawings

USE OF A PHARMACEUTICALLY ACCEPTABLE OXALATE DERIVATIVE FOR THE TREATMENT OF SKIN CONDITIONS

BACKGROUND OF THE INVENTION

The present invention relates to the use of compositions foe the treatment of conditions, disorders or diseases of the skin, the autoimmune system or the respiratory tract, or conditions, disorders or diseases associated therewith, which comprise a pharmaceutically acceptable oxalate and a pharmaceutical acceptable carrier. The pharmaceutically acceptable oxalate is preferably an oxalate of a group Ia or IIa metal or a transition metal of the first transition series.

In International Patent Application No. WO 94/15574, the present inventor disclosed that oxalates of group Ia or IIa metals could be used for restoring hair loss due to conditions such as alopecia areata. The present inventor has now discovered that inorganic and organic oxalates can also be used to treat conditions, disorders or diseases of the skin, the autoimmune system or the respiratory tract, and associated illnesses, other than those involving hair loss.

In International Patent Application No. WO92/04896, Gerber and Matkovic disclose the use of gallium compounds for treating diseases mediated by macrophage cell lines, including lupus erythematosus, and for prevention of resistance to transplantation. The preferred gallium compounds are selected from the group consisting of gallium nitrate, gallium citrate, gallium chloride, gallium carbonate, gallium acetate, gallium lactate, gallium tartrate, gallium oxalate, gallium oxide and hydrated gallium oxide. Of these compounds, gallium nitrate is especially favoured.

SUMMARY OF THE INVENTION

Accordingly, in a first aspect of the invention, there is provided the use of a composition comprising a pharmaceutically acceptable oxalate and a pharmaceutically acceptable carrier in the manufacture of a medicament for use in a method of treating an immunologically-mediated condition, disorder or disease of the skin, the autoimmune system or the respiratory tract, or a condition, disorder or disease associated therewith, wherein said composition does not comprise gallium oxalate when said condition is lupus erythematosus, and does not comprise a group Ia or IIa metal oxalate or ammonium oxalate when said condition is seborrheoa.

In a second aspect of the invention, there is provided a method of treating an immunologically-mediated condition, disorder or disease of the skin, the autoimnune system or the respiratory tract, or a condition, disorder or disease associated therewith, comprising administering to a patent a therapeutically effective amount of a composition comprising a pharmaceutically acceptable oxalate and a pharmaceutically acceptable carrier, wherein said composition does not comprise gallium oxalate when said condition is lupus erythematosus, and does not comprise a group Ia or IIa metal oxalate or ammonium oxalate when said condition is seborrheoa.

In the invention according to its first or second aspects, the conditions, disorders or diseases of the skin which may be treated with the oxalate compositions include psoriasis, eczema, dermatitis, erythema, seborrhoea, lichen planus, lupus erythematosus, herpes simplex, cutaneous manifestations of immunologically mediated diseases, hypoproliferative or inflammatory skin diseases, and related conditions. The more common forms of dermatitis which may be treated by the invention include atopic dermatitis, contact dermatitis and seborrheic dermatitis.

The associated conditions, disorders or diseases which may be treated by the invention include infections, chronic inflammatory diseases and eating-related disorders but are not restricted to such illnesses. Skin conditions are often known to be associated with disorders of the immune system and with diseases of the respiratory tract, such as asthma, and, accordingly, it is envisaged that the present invention may also be of assistance in the treatment of such complaints. In a preferred embodiment, the invention may be used in the treatment of cutaneous asthma, since treatment or any underlying skin complaint may provide relief against asthma caused by flaking or scaly skin. However, the precise mode of action of the active ingredient is not fully understood and it is also believed that the oxalate components may act directly on the immune system, either as stimulants or as immunosupressants. The present inventor has also observed that, when used for treating skin conditions in individuals with eating-related disorders, oxalate compounds may also act as appetite suppressants, perhaps by relieving stress. It is intended, therefore, that the treatment of such disorders also lies within the scope of the invention.

In a third aspect of the invention, there is provided a method for enhancing the aesthetic appearance of skin other than the scalp comprising applying to the skin a composition comprising a pharmaceutically acceptable oxalate and a pharmaceutically acceptable carrier.

DETAILED DESCRIPTION OF THE INVENTION

In the compositions used in the invention in any of its various aspects, the pharmaceutically acceptable oxalate may be an inorganic or organic oxalate. Preferably, the oxalate is an oxalate of a group Ia or IIa metal or an ammonium oxalate. The oxalate may be in the form of a double salt, such as, for example, potassium ammonium oxalate. In another embodiment, the pharmaceutically acceptable oxalate comprises a transition metal, preferably a metal selected from the first transition series. In this last embodiment, zinc or iron oxalates have been found to be particularly efficacious.

The inorganic oxalate may be used in admixture with naturally occurring organic oxalates, such as oxalates found in extracts obtained from vegetables and plants, such as squill and aloe species. The oxalates in such vegetable and plant extracts may occur in association with naturally-occurring mucilaginous carbohydrates, gums, resins or the like and may used in conjunction with such substances. In some plant extracts, it has been found that calcium oxalate occurs as crystals which pierce and intensely irritate the skin. Calcium oxalate crystals should, therefore, be crushed to at least fine particle size, prior to use, whether or not they are to be used in conjunction with associated carbohydrate mucilage.

The pharmaceutically acceptable carrier may be aqueous or alcoholic in nature and may include a viscous base to retain the composition in situ in use. Suitable diluents for use as carriers to form a lotion include water and lower alcohols or polyols, such as methanol, ethanol, isopropanol, glycerol or propylene glycol. In order to form a cream or an ointment, a paraffinic fraction and an emulsion base may be used. The carrier may also comprise other conventional carriers or diluents, such as, for example, glucose, lactose, corn starch, starch paste, gum acaia, gelatin, mannitol, magnesium trisilicate, potato starch, urea, keratin or colloidal silica. The composition may further comprise other compounds, such as proteins, amino acids, minerals, vitamins, carbohydrates, essential oils, colouring agents or perfumes.

The vehicle or diluent in compositions for topical application may be in the form of an ointment, a cream or a lotion. The vehicle is important in such treatments, since excessive dilution may affect the stability of some creams and, of course, it is necessary to maintain contact of the active oxalate with the skin or affected area to be treated. Cream and ointment bases may be selected to have both hydrophilic and lipophilic properties. Although the vehicle is primarily intended to carry the active oxalate compound, it may itself have a beneficial effect by determining how moist the skin is and how well the drug penetrates to the lower layers of skin or dermis. The vehicle may be selected to have its own anti-inflammatory or soothing effect in the condition to be treated, such as, for example, in the treatment of eczema or psoriasis.

Eczema is a form of dermatitis characterised by itchy, red, scaly skin, in which tiny blisters form that leave a raw surface when scratched. The skin may become infected at this stage, usually with bacteria, and the skin eventually becomes thickened with the outer layer constantly flaking off in the form of scales. Psoriasis is a chronic and sometimes distressing skin condition that can recur for no obvious reason, although attacks may be triggered by stress, skin damage or infection by streptococcal and other bacteria.

For dry scaling skin conditions, such as atopic eczema, an emollient preparation consisting of a mixture of water, waxes and oils to soothe and moisten the skin may be used. The emollient preparation can be applied in the form of a cream, an ointment or a lotion. In many conditions, aqueous creams provide a simple, effective and inexpensive vehicle for the active oxalates, since the former are substantially free of ingredients that can cause sensitisation.

Some conventional preservatives, such as benzylparaben, may worsen an existing condition by causing contact allergic dermatitis and should be avoided in creams for certain conditions, as should certain emollient ingredients, such as lanolin. Urea cream is useful for moisturising scaly skin and may be helpful for treating infants or elderly patients suffering from eczema. Typically, urea creams for use in the present invention might contain sodium oxalate or zinc oxalate in amounts of 3 to 10% as active ingredient.

Depending upon the size of the affected area and the severity of the skin disorder in individual cases, the recommended amount of oxalate in the composition is between 1–10% by weight. Amounts over 5% may be utilised only under medical supervision. Care should of course be taken to prevent any microbial contamination or contact of the composition with the eyes or other sensitive areas of the patient. Citric acid, preferably in the form of lime juice, may be used to reduce the irritation caused when the composition is applied to the afflicted part. No side effects or instability of the applied compositions have been observed.

The amount of active ingredient as well as the frequency of application may be varied according to condition, disorder or disease to be treated and the individual concerned. Compositions for treating mild eczema in a child, for example, would contain correspondingly reduced amounts of the active oxalate compounds compared with compositions for treating severe eczema in an adult. The exact proportions of oxalate and carrier in the composition suitable for treating a particular condition or disease must be determined on an individual basis in accordance with standard treatment regimes. For ease of application, the composition is preferably in a semi-solid or semi-liquid form, containing one or more of the active oxalate compounds. Generally, the active principle is included in a lotion or an ointment in an amount of 0.1–10% by weight but, more usually, in the order of 1–5% by weight. Amounts of up to 10% or more may be utilised in certain circumstances, however, under medical supervision.

The present invention includes compositions adapted for topical application to the human skin. Conventional pharmaceutical formulations suitable for this purpose includes ointments, lotions, pastes, jellies, gels, mousses, sprays, foams, aerosols and other similar preparations. The term "ointment" is understood to include creams having oleaginous or water-soluble, emulsion bases, such as, for example, lanolin, petrolatum, glycols, glycerin and the like. The compositions may be liposomal preparations or lipid emulsions or may be dissolved in conventional solvents, such as acetonitrile, dimethylformamide, DMA, alcohol, propanol and the like. The percentages by weight of the oxalates utilised typically range from about 0.1% to about 10% of the pharmaceutical preparation, preferably from 0.75% to about 4.95%. In these preparations, the aforesaid pharmaceutical carrier is suitable for topical application and is recommended that the composition be used on a regular basis and for a period of time sufficient to effect treatment.

The invention will now be described by way of illustration only in the following examples:

EXAMPLE I

An ointment composition in accordance with the invention was formed as follows:

| | |
|---|---|
| White soft paraffin B.P. | 15.0% |
| Light liquid paraffin PHEUR | 13.0% |
| Hypoallergenic anhydrous lanolin | 1.0% |
| Emulsion base | 58.0% |
| Plant derived calcium oxalate with approx. equal weight of mucilage | 6.0% |
| Citric acid | 3.0% |
| Fructose | 2.0% |
| Glucose | 2.0% |

EXAMPLE II

An ointment composition in accordance with the invention was formed as follows:

| | |
|---|---|
| White soft paraffin BP | 15.0% |
| Light liquid paraffin PHEUR | 13.0% |
| Hypoallergenic anhydrous lanolin | 1.0% |
| Emulsion base | 64.0% |
| Calcium oxalate B.P. as a fine powder | 3.25% |
| Sodium oxalate B.P. | 1.75% |
| Glucose/Carbohydrate | 2.0% |

EXAMPLE III

A paste composition in accordance with the invention was formed as follows:

| | |
|---|---|
| White soft paraffin B.P. | 48.0% |
| Zinc oxide | 24.0% |
| Starch | 24.0% |
| Calcium oxalate B.P. as a fine powder | 0.45% |
| Zinc oxalate B.P. | 2.15% |
| Sodium oxalate B.P. | 1.40% |

EXAMPLE IV

A cream composition in accordance with the invention was formed as follows:

| | |
|---|---|
| Zinc oxide | 6.975% |
| Castor oil | 46.5% |
| Cetostearyl alcohol | 1.86% |
| White beeswax | 9.3% |
| Arachis oil | 28.365% |
| Calcium oxalate B.P. | 1.0% |
| Sodium oxalate B.P. | 2.0% |
| Zinc oxalate B.P. | 4.0% |

EXAMPLE V

Each of the compositions in examples I–IV were used to treat patients suffering from a variety of skin conditions or disorders. The paste composition of example III was used in treating circumscribed lesions in patients suffering from chronic eczema, whilst the remaining compositions were used in treating patients suffering from psoriasis and milder forms of eczema. E45, a propriety anti-dermatitis cream, was applied as a control to a separate group. In each case, the composition was initially applied twice daily to the affected areas for the first week, reducing to once a day or less as the condition improved. The ointment was applied sparingly over the afflicted area. It was found that all patients treated in accordance with the invention showed considerable improvement relative to the the control group within 24–48 hours of treatment being commenced. The improvement manifested itself in a marked decrease in the itching suffered by patients and a sharp decrease in the severity of the lesions. The effectiveness of the compositions is believed to be due, at least in part, to the notable reduction in itchiness and associated desire to scratch the afflicted area, which can in many cases exacerbate the underlying condition.

There appeared to be no statistically significant difference between the results obtained with the compositions of examples I to IV, all working equally well in the individuals concerned.

It is apparent that, even after a few days of using the oxalate compositions according to the invention, therefore, any problematic condition of the skin seems to recede, leaving the skin healthy and without abnormal scale formation. It is evident that the compositions have a cleansing effect on the skin, with the skin being kept not too greasy or too dry.

EXAMPLE VI

A cream comprising 1% calcium oxalate in an E45 base was used to treat a girl aged 14 suffering from trichotillomania and an associated eating disorder. The cream was applied topically to the scalp twice daily, in order to encourage hair regrowth in the manner described in International Patent Application No. WO 94/15574.

Within 4–6 weeks of treatment being commenced, fine downy hair was observed to be growing on the scalp. At the same time, however, it was unexpectedly observed that the incidence and severity of episodes of uncontrollable eating compulsions were greatly reduced.

It has been noted by the present inventor that patients suffering from skin disorders are frequently in a poor state of general health. For example, patients suffering from chronic skin conditions are often prone to other conditions or disorders, such as respiratory problems. Whilst the mode of action of the oxalate compositions described herein is not fully understood, it is believed that such compositions may act systemically to restore normal immune function, possibly by inhibiting binding of a natural substrate to a receptor or an enzyme involved in an inflammatory process. The inventor has observed, for example, that, even after treatment of eczema or psoriasis with oxalate compositions has ended, the condition often continues to show improvement on its own, without further medication and with no tendency for relapse. It is possible, therefore, that the oxalate compositions act to correct an underlying imbalance in the immune system and to restore the patient to a more healthy condition.

What is claimed is:

1. A method of treating an immunologically-mediated skin condition, disorder or disease, or a condition, disorder or disease associated therewith, comprising administering to a patient a therapeutically effective amount of a composition comprising a pharmaceutically acceptable oxalate and a pharmaceutically acceptable carrier, wherein said composition does not comprise a group Ia or IIa metal oxalate or ammonium oxalate when said condition is seborrhoea.

2. A method as claimed in claim 1, wherein the condition, disorder or disease of the skin includes at least one of herpes simplex, hyperproliferative skin diseases and disorders associated therewith.

3. A method as claimed in claim 2, wherein the skin condition, disorder or disease is selected from the group consisting of atopic dermatitis, contact dermatitis and seborrheic dermatitis.

4. A method as claimed in claim 1, wherein the disease is cutaneous asthma.

5. A method as claimed in claim 1, wherein the associated condition, disorder or disease is an infection or a chronic inflammatory disease.

6. A method as claimed in claim 1, wherein the pharmaceutically acceptable oxalate is an inorganic oxalate.

7. A method as claimed in claim 6, wherein the pharmaceutically acceptable oxalate is an oxalate of a group Ia or IIa metal or an ammonium oxalate.

8. A method as claimed in claim 6, wherein the pharmaceutically acceptable oxalate comprises a transition metal.

9. A method as claimed in claim 8, wherein the metal is selected from the first transition series.

10. A method as claimed in claim 9, wherein the metal is zinc or iron.

11. A method as claimed in claim 1, wherein the pharmaceutically acceptable oxalate is an organic oxalate.

12. A method as claimed in claim 11, wherein the organic oxalate is present in admixture with an inorganic oxalate selected from the group consisting of a group Ia or IIa metal, ammonium oxalate, and a transition metal.

13. A method as claimed in claim 1, wherein the pharmaceutically acceptable carrier is selected from the group consisting of water, glucose, lactose, corn starch, starch paste, gum acacia, gelatin, mannitol, magnesium trisilicate, potato starch, urea, keratin, colloidal silica and a lower alcohol.

14. A method as claimed in claim 1, wherein the pharmaceutically acceptable carrier further comprises a paraffin fraction or an emulsion base.

15. A method as claimed in claim 1, wherein the pharmaceutically acceptable oxalate is derived from a vegetable or plant extract.

16. A method as claimed in claim 15, wherein the oxalate is associated with a naturally occurring gum, resin, mucilaginous carbohydrate or the like.

17. A method as claimed in claim 1, wherein the composition is formulated for topical application.

18. A method as claimed in claim 1, wherein the composition is formulated as a tablet, a pellet, a capsule or a suppository.

19. A method as claimed in claim 1, wherein the composition further comprises a protein, an amino acid, a mineral, a carbohydrate, a vitamin, an essential oil, a colouring agent or a perfume.

20. A method for enhancing the aesthetic appearance of skin other than the scalp comprising applying to the skin a composition comprising a pharmaceutically acceptable oxalate and a pharmaceutically acceptable carrier, wherein the pharmaceutically acceptable oxalate comprises a transition metal.

21. A method as claimed in claim 20, wherein the metal is selected from the first transition series.

22. A method as claimed in claim 21, wherein the metal is zinc or iron.

23. A method as claimed in claim 20, wherein the pharmaceutically acceptable oxalate further comprises an organic oxalate.

24. A method as claimed in claim 20, wherein the pharmaceutically acceptable carrier is selected from the group consisting of water, glucose, lactose, corn starch, starch paste, gum acacia, gelatin, mannitol, magnesium trisilicate, potato starch, urea, keratin, colloidal silica and a lower alcohol.

25. A method as claimed in claim 20, wherein the pharmaceutically acceptable carrier comprises a paraffin fraction or an emulsion base.

26. A method as claimed in claim 23, wherein the pharmaceutically acceptable organic oxalate is derived from a vegetable or plant extract.

27. A method as claimed in claim 26, wherein the organic oxalate is associated with a naturally occurring gum, resin, mucilaginous carbohydrate or the like.

28. A method as claimed in claim 20, wherein the composition is formulated for topical application.

29. A method as claimed in claim 20, wherein the composition is formulated as a tablet, a pellet, a capsule or a suppository.

30. A method as claimed in claim 20, wherein the composition further comprises a protein, an amino acid, a mineral, a carbohydrate, a vitamin, an essential oil, a colouring agent or a perfume.

31. A method as claimed in claim 2, wherein the cutaneous manifestation of an immunologically-mediated disease is selected from the group consisting of psoriasis, eczema, dermatitis, erythema, seborrhoea, lichen planus and lupus erythematosus.

32. A method as claimed in claim 2, wherein the hyperproliferative skin disease is one of psoriasis, and conditions, disorders or diseases associated therewith.

* * * * *